United States Patent
Mohapatra et al.

(10) Patent No.: US 11,518,727 B2
(45) Date of Patent: Dec. 6, 2022

(54) COMMERCIALLY VIABLE PROCESS FOR PREPARATION OF ARYL KETONES

(71) Applicant: ANTHEA AROMATICS PRIVATE LIMITED, Navi Mumbai (IN)

(72) Inventors: Manoj Kumar Mohapatra, Navi Mumbai (IN); Ramamohanrao Bendapudi, Navi Mumbai (IN); Paul Vincent Menacherry, Mumbai (IN); Vincent Paul, Mumbai (IN)

(73) Assignee: ANTHEA AROMATICS PRIVATE LIMITED, Navi Mumbai (IN)

( * ) Notice: Subject to any disclaimer, the term of this patent is extended or adjusted under 35 U.S.C. 154(b) by 0 days.

(21) Appl. No.: 17/432,672

(22) PCT Filed: Apr. 13, 2019

(86) PCT No.: PCT/IB2019/053058
§ 371 (c)(1),
(2) Date: Aug. 20, 2021

(87) PCT Pub. No.: WO2020/174271
PCT Pub. Date: Sep. 3, 2020

(65) Prior Publication Data
US 2022/0169588 A1    Jun. 2, 2022

(30) Foreign Application Priority Data
Feb. 28, 2019    (IN) .............................. 201921007903

(51) Int. Cl.
*C07C 45/46*    (2006.01)
*C07C 45/45*    (2006.01)

(52) U.S. Cl.
CPC .................................. *C07C 45/455* (2013.01)

(58) Field of Classification Search
CPC .............................. C07C 45/455; C07C 45/46
See application file for complete search history.

(56) References Cited

U.S. PATENT DOCUMENTS

| | | | |
|---|---|---|---|
| 2,483,566 A | 10/1949 | Thompson | |
| 5,041,616 A | 8/1991 | Sumner, Jr. | |
| 5,962,743 A | 10/1999 | Gruber et al. | |

FOREIGN PATENT DOCUMENTS

| | | |
|---|---|---|
| DE | 2616583 | 10/1976 |
| EP | 0075390 | 3/1983 |
| EP | 0241306 | 10/1987 |
| GB | 1164046 | 9/1969 |
| WO | 01/36363 | 5/2001 |

OTHER PUBLICATIONS

International Search Report and Written Opinion issued by the EPO for PCT/IB2019/053058 dated Nov. 8, 2019.
Volume edited by Clayton H. Heathcock of the University of California, Berkeley, CA, USA "Comprehensive Organic Synthesis", vol. 2, 1991, pp. 707-731.
Yamoto et al., "CSK: a Protein-tyrosine Kinase Involved in Regulation of src Family Kinases", The Journal of Chemistry, 1991.
Mona Hosseini Sarvari, Hashem Sharghi, "Synthesis (13), 2165-2168 (2004), Simple and Improved Procedure for the Regioselective Acylation of Aromatic Ethers with Carboxylic Acids on the Surface of Graphite in the Presence of Methanesulfonic Acid", Department of Chemistry, Faculty of Science, Shiraz University, Shiraz 71454, Iran.
Mark C. Wilkinson "Greener" Friedel—Crafts Acylations: A Metal- and Halogen-Free Methodology, Org. Lett. 2011, 13, 9, 2232-2235 Publication Date: Mar. 25, 2011.
Hossein Naeimi, Abdol Hamid Raesi, Mohsen Moradian,"Solvent-free direct ortho C-acylation of phenolic systems by methanesulfonic acid as catalyst" Department of Organic Chemistry, Faculty of Chemistry, University of Kashan, Kashan, 87317, I.R.Iran. Iranian J. Catalysis 1 (2), 65-70 (2011).

*Primary Examiner* — Sikarl A Witherspoon
(74) *Attorney, Agent, or Firm* — Silvia Salvadori

(57) ABSTRACT

The present disclosure provides a process for preparing an aryl ketone of Formula I, comprising reacting a substituted benzene of Formula II with a carboxylic acid of formula IIIa and/or a carboxylic anhydride of formula IIIb in presence of an alkyl sulfonic acid acting as catalyst cum solvent/contacting medium. I, II, IIIa, IIIb, wherein, $R_1$, $R_2$, $R_3$ and $R_4$ are as defined in the description.

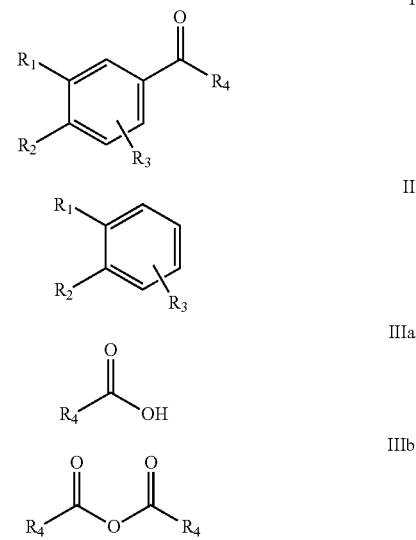

9 Claims, No Drawings

COMMERCIALLY VIABLE PROCESS FOR PREPARATION OF ARYL KETONES

TECHNICAL FIELD OF THE INVENTION

The present disclosure pertains to technical field of organic synthesis, in particular to an improved and commercially viable process for preparation of aryl ketones.

BACKGROUND OF THE INVENTION

Aryl ketones are both valuable intermediates and end products (active ingredients) in a vast array of high-value added products, which include pharmaceuticals, agrochemicals, biocides, flavours & fragrances, antioxidants and fine chemicals.

Aryl ketones typically are prepared by the reaction of an aromatic compound with the corresponding carboxylic acid anhydride or the carboxylic acid chloride in the presence of a corrosive Lewis acid (such as $AlCl_3$, $FeCl_3$, $SnCl_4$, $TiCl_4$, $BF_3$, $ZnCl_2$) or Bronsted acids (such as HF, PPA, $H_2SO_4$) as catalyst. Disadvantages associated with this approach include the use of toxic and corrosive acid halides as the acylating agents. When the acyl reactant is an acyl halide, the catalyst used is typically a Lewis acid such as $AlCl_3$ or $ZnBr_2$. When the acyl reactant is a carboxylic acid, the catalyst used is typically a protic acid, such as Hydrogen fluoride or Polyphosphoric acid.

During the workup of acylation mixtures of this type the Friedel-Crafts catalysts are destroyed by hydrolysis and produce relatively large amounts of hydrochloric acid in the effluent along with the formation of huge amount of sludge. Aluminum chloride, the most effective and commonly used Lewis Acid reagent for this reaction, is an unpleasant, hazardous material to handle. Large quantities of aluminum chloride, at least stoichiometric, are usually needed for the said acylation. In some acylation reactions two or three times the stoichiometric amount of aluminum chloride has to be used, which generates aluminium oxychloride species upon hydrolysis with water. Also, the hydrochloric acid produced as by-product needs to be neutralized or otherwise disposed of, which makes this process highly polluting and environmentally harmful.

Also, in case the acyl halide reactant such as an acyl chloride is used, this must be first prepared from the carboxylic acid, typically using a reagent like thionyl chloride that is not a particularly desirable compound to handle on large scale. Hydrogen chloride gas is released during the formation of the acyl chloride (along with $SO_2$ when using Thionyl chloride) and in the acylation reaction must be abated with an acid gas scrubber.

Also, the solvent of choice for many such conventional Friedel-Crafts acylation processes is a chlorinated hydrocarbon, such as dichloromethane or ethylene dichloride, whose use in industrial synthesis has become increasingly less acceptable.

Another reported method used to prepare said aryl ketone involves the condensation of a carboxylic acid derivative with an active aromatic compound. Carboxylic acids are preferred starting materials because they are less expensive and less corrosive than the corresponding carboxylic acid anhydrides or carboxylic acid chlorides.

For example, British Patent 1,164,046 discloses the preparation of aryl ketones by aromatic acylation using a carboxylic acid and liquid hydrogen fluoride as the condensing agent. The disadvantage associated with this process is the use of liquid hydrogen fluoride which presents severe toxicity, corrosion and handling problems.

European Patent Application 87-303,162 discloses the preparation of diaryl ketones (benzophenones) comprising contacting an aromatic compound with an aromatic carboxylic acid or an acid chloride thereof in the presence of a strong acid such as Trifluoromethanesulfonic acid and a weak acid (equal to Chloroacetic acid) as solvent. A disadvantage to this method is that the solvent cannot be reused without drying.

European Patent Application 82-304,341 similarly discloses the reaction of an aromatic carboxylic acid with an aromatic compound in the presence of a stoichiometric amount of a fluoroalkane sulfonic acid to obtain diaryl ketones.

U.S. Pat. No. 5,041,616 discloses the preparation of aryl ketones comprising contacting an aromatic compound with a carboxylic acid in the presence of a catalytic amount of an organic sulfonic acid while removing the water of reaction as an azeotrope from the reaction mixture. However the disadvantage associated with this process is the additional unit operation of azeotropic distillation to remove the water liberated in the reaction, since otherwise reaction does not proceed to the required extent, which results in lower yields, since the substrate subjected to higher temperatures under acidic conditions.

German patent application 26 16 583, discloses the preparation of aryl ketones comprising reaction of non-hydroxylated aromatic compounds with a carboxylic acid or a carboxylic acid anhydride in the vapour phase at 250° C. to 500° C. in the presence of an acid silica/alumina catalyst having a surface area of at least 50 m3/g. However, with this process using amorphous or crystalline silica/alumina catalysts undesired by-products of very different structures are formed, for example in the case of the reaction of Benzene with Benzoic acid, biphenyl, diphenylmethane and alkylated benzenes are also formed in addition to the desired benzophenone. A particularly serious disadvantage of this process is the short life of the catalysts; thus, the amount of the desired Benzophenone drops considerably if the reaction time is increased to 24 hours.

U.S. Pat. No. 5,962,743 discloses a process for preparing aryl ketones comprising reaction of an aromatic compound with a carboxylic acid in the presence of a reaction medium comprising polyphosphoric acid and a strong protic acid, wherein the strong protic acid is methane sulfonic acid. However, this method does not provide for a method for recovery and reuse of the polyphosphoric acid and methane sulfonic acid.

Comprehensive Organic Synthesis, Volume 2, 1991, Pages 707-731, has disclosed that polyphosphoric acid in the presence of protic acid is most frequently used, but suffers from several well-known disadvantages, particularly on scale-up. Its extreme viscosity requires that reactions to be carried out at elevated temperatures to permit stirring, and it is a poor solvent for organic substrates. Hydrolysis during work-up is often tedious.

Yamoto et al., 1991, have reported the use of phosphorus pentoxide in methane sulfonic acid as a more convenient reagent for dehydrative cyclization of lactones and unsaturated carboxylic acids, being a mobile liquid with good solvent properties.

Synthesis (13), 2165-2168 (2004) discloses acylation of aromatic compounds such as Anisole using aliphatic & aromatic carboxylic acids in presence of a combination of graphite with MSA, while no reaction was observed in the presence either graphite or MSA.

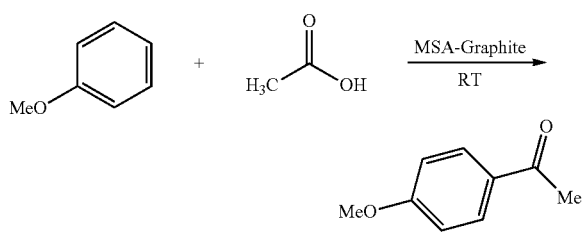

*Org. Lett.*, 2011, 13 (9), pp 2232-2235, "Greener" Friedel-Crafts Acylations discloses utility of methanesulfonic anhydride for promoting the Friedel-Crafts acylation reaction of aryl and alkyl carboxylic acids using toluene as solvent.

Iranian J. Catalysis 1(2), 65-70 (2011) discloses solvent free ortho acylation of phenols and naphthols with different organic acids in the presence of methanesulfonic acid as a Bronsted acid. Although the said reference refers to a solvent free reaction but as per the disclosure provided therein the said process comprises use of excessive carboxylic acid (1:5 m/m of substrate:carboxylic acid) and the catalytic amount of methane sulfonic acid (0.4 mol). However, this neither mentions nor teaches or indicate to a person skilled in the art about the possibility of recovery of carboxylic acid nor of its reuse, thus making the process commercially unattractive.

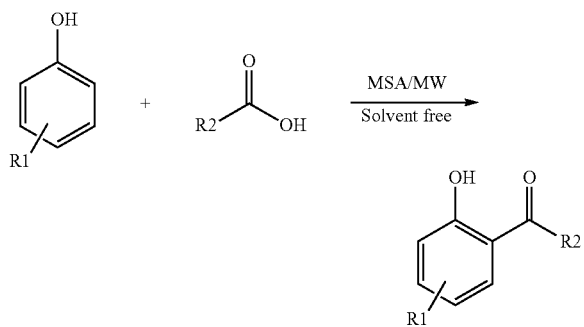

*Asian* J. Chemistry: 29 (4), 749-754 (2017) discloses synthesis of 4, 6-diacetylresorcinol comprising contacting resorcinol with acetic acid in presence of MSA and $P_2O_5$.

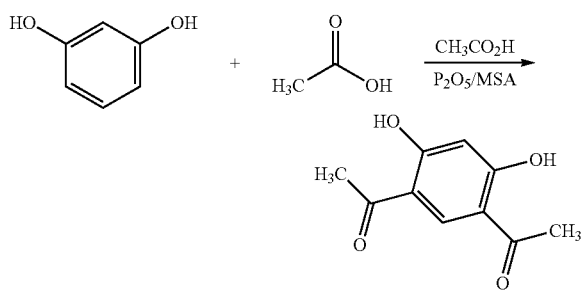

However, the above examples do not allow the efficient recovery and re-use of the solvent/contacting medium, and also generate large amounts of effluent during work-up.

The problems typically associated with the prior art are summarized as follows:

1. The conventional Friedel-Crafts aromatic acylation typically utilizes an acyl halide reactant, usually an acyl chloride. This must be first prepared from the carboxylic acid, typically using a reagent like thionyl chloride that is not a particularly desirable compound to handle on large scale. Hydrogen chloride gas, is released in the formation of formation of the acyl chloride (along with $SO_2$ when using thionyl chloride) and in the acylation reaction and must be abated with an acid gas scrubber.
2. The conventional Friedel-Craft acylation generates a large volume of waste, especially when acylation is done using acyl chlorides and/or in presence of corrosive Lewis acid catalysts.
3. Also, the solvent of choice for many such conventional Friedel-Crafts acylation processes is a chlorinated hydrocarbon, such as dichloromethane or ethylene dichloride, whose use in industrial synthesis has become increasingly less acceptable.
4. Use of excessive quantity of carboxylic acid and/or its corresponding anhydride to act as contacting medium and/or
5. The use of Polyphosphoric acid and the like as contacting medium have the disadvantage of having a high viscosity of the reaction mixture thus requiring the reaction to be carried out at high temperatures.
6. Still other methods previously disclosed require extra unit operations like azeotropic distillation to remove the water formed in the reaction, to take the target reaction in the forward direction.

In recent years, much of the research efforts are devoted towards developing "greener" or sustainable technologies for pharma and fine chemical products involving C—C bond forming steps. While there are exciting developments in heterogeneous catalysis, there is still a need for an improved and environmentally friendly method suitable for batch manufacturing of aryl ketones, especially for those involving the Friedel-Crafts acylation.

In view of the shortcomings in the prior art regarding the health, safety and environment aspects of conventional Friedel-Crafts acylation, there is a dire need to find a process which is both environmentally friendly and commercially viable to carry out the said acylation reactions. Also it is becoming increasingly important to provide economically feasible processes for recycling key raw materials.

The present invention satisfies the existing needs, as well as others, and generally overcomes the deficiencies found in the prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

OBJECTS OF THE INVENTION

The primary object of this invention is to provide an economical, efficient and environmentally friendly process for preparation of substituted aryl ketones, which minimizes effluent generation issues faced when using conventional Friedel-Craft acylation.

A further object of this invention is to provide a process for preparation of substituted aryl ketones that avoids use of aluminum chloride and other Lewis Acid reagents conventionally used for Friedel-Crafts aromatic acylation.

Yet another object of this invention is to provide an efficient process for preparation of substituted aryl ketones, wherein acylation is carried out using carboxylic acid and/or corresponding carboxylic acid anhydride, rather than using an acyl halide.

A further object of the present invention is to provide a method for efficient recycling and re-use of reagents and catalyst cum solvent/contacting medium used in process of preparation of substituted aryl ketones.

Various objects, features, aspects and advantages of the inventive subject matter will become more apparent from the following detailed description of preferred embodiments.

SUMMARY

Aspects of the present invention relate to an efficient, economical, industrially viable and environmentally friendly process for preparation of a substituted aryl ketone of Formula I in substantially pure form and high yield, comprising contacting a substituted benzene of Formula II with a carboxylic acid of Formula IIIa and/or corresponding carboxylic acid anhydride of Formula IIIb in presence of an alkyl sulfonic acid which acts as a catalyst and a solvent/medium for contacting the reaction contents, the said alkyl sulfonic acid characterised by its ability to be easily recovered and reused multiple times for carrying out the reaction;

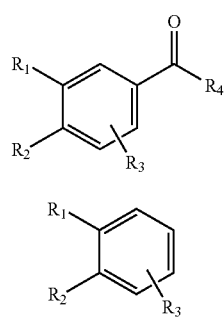

wherein $R_1$, $R_2$ and $R_3$ are independent of each other, $R_1$ represents H, R or —OR, wherein R is a substituted or unsubstituted $C_1$-$C_4$ alkyl group, substituted or unsubstituted $C_3$-$C_6$ cycloalkyl group, $R_2$ represents hydroxy group —OH, or alkoxy group —OR, wherein R is a substituted or unsubstituted $C_1$-$C_4$ alkyl group, substituted or unsubstituted $C_3$-$C_6$ cycloalkyl group, or where $R_1$ and $R_2$ together jointly forms an alkylenedioxy group represented by —O—$(CH_2)_n$—O— wherein n is 1, 2 or 3, and $R_3$ is a substituent at any position of aromatic ring other than position 1, 3 and 4 and represents H, R, —OR, wherein R is a substituted or unsubstituted $C_1$-$C_4$ alkyl group or substituted or unsubstituted $C_3$-$C_6$ cycloalkyl group, $NH_2$ or SH, and the carboxylic acid of Formula IIIa and/or the corresponding carboxylic acid anhydride of Formula IIIb are as represented below,

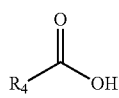

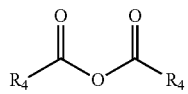

wherein $R_4$ represents, $R_6$, $XR_6$, (wherein $R_6$ is a substituted or unsubstituted $C_1$-$C_8$ alkyl group and X represents Cl, Br or Iodine substituted on $C_1$-$C_8$ carbon) or Ar—($R_6$, $OR_6$, OH or X substituted phenyl & naphthyl rings).

According to embodiments of the present disclosure, the alkyl sulfonic acid used in the process of the present disclosure can be represented by a compound of Formula IV which acts as a catalyst and a solvent/medium for reacting the substituted benzene of Formula II with a carboxylic acid of Formula IIIa and/or corresponding carboxylic acid anhydride of Formula IIIb, to generate the corresponding aryl ketone of Formula I generating by-products such as water and/or the corresponding carboxylic acid, respectively, wherein the alkyl sulfonic acid together with unreacted carboxylic acid is easily separated from the product of Formula I and unreacted substrate of Formula II at the end of the reaction by dilution with water, and substantially recovered and reused.

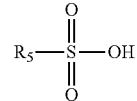

wherein $R_5$ represents an alkyl group such as methyl, ethyl or propyl.

The process of the present invention is also characterised by the recovery of excess carboxylic acid used and/or generated in the reaction when anhydride of Formula IIIb is used. Thus the present invention also relates to the field of recovery and the reuse of the solvent/contacting medium, and the recovery of excess carboxylic acid used and/or generated in the reaction, thereby making the process economical, efficient, industrially viable and environmentally friendly.

In a more preferred embodiment, the alkyl sulfonic acid of Formula IV can be methanesulfonic acid (MSA) of Formula V, which acts as both catalyst and as solvent/contacting medium for the acylation reaction, and is recovered and reused multiple times without significant material loss or loss of activity. Besides being an effective catalyst as well as solvent/contacting medium for the acylation reaction, the use of methane sulfonic acid is especially attractive from an economic and environmental standpoint as it is derived from biomass.

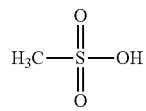

The process disclosed in the present invention may be advantageously used for industrial manufacture of several important aryl ketones as disclosed herein below.

The aryl ketones thus obtained can be used as is, or as intermediates to make a variety of industrially important products such as anethole (from 4-Methoxy propiophenone), dihydrosafrole (from 3,4-Methylenedioxypropiophenone) and isoeugenol (from 1-(4-Hydroxy-3-methoxyphenyl) propanone), among others.

DETAILED DESCRIPTION OF INVENTION

The following is a detailed description of embodiments of the present disclosure. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

Unless the context requires otherwise, throughout the specification which follow, the word "comprise" and variations thereof, such as, "comprises" and "comprising" are to be construed in an open, inclusive sense that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

In some embodiments, the numbers expressing quantities of ingredients, properties such as concentration, process conditions, and so forth, used to describe and claim certain embodiments of the invention are to be understood as being modified in some instances by the term "about." Accordingly, in some embodiments, the numerical parameters set forth in the written description are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable.

The recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

The headings and abstract of the invention provided herein are for convenience only and do not interpret the scope or meaning of the embodiments.

Various terms are used herein. To the extent a term used in a claim is not defined below, it should be given the broadest definition persons in the pertinent art have given that term as reflected in printed publications and issued patents at the time of filing.

In a general embodiment of the present invention, the inventors of the present invention have disclosed a process wherein an alkyl sulfonic acid is used as catalyst cum solvent/contacting medium to facilitate reaction of a substituted benzene of Formula II with a carboxylic acid of Formula IIIa and/or corresponding carboxylic acid anhydride of Formula IIIb, to generate corresponding aryl ketone of Formula I.

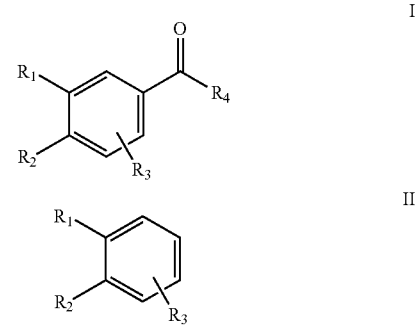

wherein $R_1$, $R_2$ and $R_3$ are independent of each other, $R_1$ represents H, R or —OR, wherein R is a substituted or unsubstituted $C_1$-$C_4$ alkyl group, substituted or unsubstituted $C_3$-$C_6$ cycloalkyl group, $R_2$ represents hydroxy group —OH, or alkoxy group —OR, wherein R is a substituted or unsubstituted $C_1$-$C_4$ alkyl group, substituted or unsubstituted $C_3$-$C_6$ cycloalkyl group, or where $R_1$ and $R_2$ together jointly forms an alkylenedioxy group represented by —O—$(CH_2)_n$—O— wherein n is 1, 2 or 3, and $R_3$ is a substituent at any position of aromatic ring other than position 1, 3 and 4 and represents H, R, —OR, wherein R is a substituted or unsubstituted $C_1$-$C_4$ alkyl group or substituted or unsubstituted $C_3$-$C_6$ cycloalkyl group, $NH_2$ or SH, and the carboxylic acid of Formula IIIa and/or the corresponding carboxylic acid anhydride of Formula IIIb are as represented below,

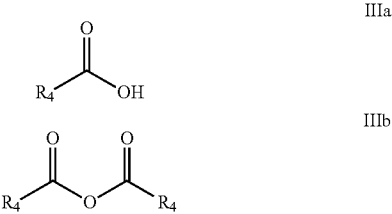

wherein $R_4$ represents, $R_6$, $XR_6$, (wherein $R_6$ is a substituted or unsubstituted $C_1$-$C_8$ alkyl group and X represents Cl, Br or Iodine substituted on $C_1$-$C_8$ carbon) or Ar—($R_6$, $OR_6$, OH or X substituted phenyl & naphthyl rings).

According to embodiments of the present disclosure, the alkyl sulfonic acid used in the process of the present disclosure can be represented by a compound of Formula IV which acts as both catalyst and as solvent/medium for reacting the substituted benzene of Formula II with a carboxylic acid of Formula IIIa and/or corresponding carboxylic acid anhydride of Formula IIIb, to generate the aryl ketones of Formula I.

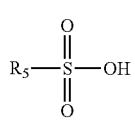

IV wherein $R_5$ represents an alkyl group such as methyl, ethyl or propyl.

In a preferred embodiment, the alkyl sulfonic acid of Formula IV can be methane sulfonic acid, ethane sulfonic acid or propane sulfonic acid.

In a more preferred embodiment, the alkyl sulfonic acid of Formula IV can be methane sulfonic acid (MSA) of Formula V, which acts as both catalyst and solvent/contacting medium for the acylation reaction, and is recovered and reused multiple times without significant material loss or loss of activity. Besides being an effective catalyst as well as solvent/contacting medium for the acylation reaction, the use of methane sulfonic acid is especially attractive from an economic and environmental standpoint as it is derived from biomass.

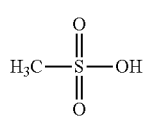

V

The term "solvent/contacting medium" is used herein in the conventional sense, and refers to a liquid medium in which the substituted benzene of Formula II and the carboxylic acid of Formula IIIa and/or corresponding carboxylic acid anhydride of Formula IIIb react to produce the corresponding substituted aryl ketone of Formula I.

At the end of the reaction, the alkylsulfonic acid used herein is easily separated from the substituted aryl ketone of Formula I and the substituted benzene of Formula II, by dilution with water, whereby the product and unreacted substituted benzene substrate remain in the organic phase, and the alkyl sulfonic acid together with unreacted carboxylic acid are separated in the aqueous phase, and are easily recovered and purified using conventional techniques such as distillation.

The inventors of the present invention have observed that the quantity of alkyl sulfonic acid required for use as catalyst cum solvent/reaction medium is generally in excess of 2.0 moles per mole of substituted benzene substrate of formula II, and the optimum usage of alkyl sulfonic acid is between 3.0 and 16.0 moles per mole of substituted benzene substrate of formula II, beyond which typically no significant cost-benefit advantage was observed.

The inventors of the present invention disclose herein that the use of methane sulfonic acid is preferred since it can be easily recovered and reused multiple times without significant material loss or loss of activity. Moreover, the use of methane sulfonic acid is especially attractive as it is derived from biomass.

The general embodiment of the process disclosed for the preparation of aryl ketone of Formula I comprises:

i. contacting substituted benzene of Formula II with a carboxylic acid of Formula IIIa and/or its corresponding anhydride of Formula IIIb in presence of an alkylsulfonic acid which acts as catalyst cum solvent/contacting medium, to form in a reaction mass an aryl ketone of Formula I;

ii. dilution of the reaction mass with water at the end of the reaction to separate the alkylsulfonic acid together with unreacted carboxylic acid in aqueous phase, and the substituted aryl ketone of Formula I and unreacted substituted benzene of Formula II in organic phase.

iii. purification of the aryl ketone of Formula I and recovering the unreacted benzene substrate of Formula II separated in the organic phase using conventional techniques such as distillation, crystallization, and the like, to obtain the aryl ketone of Formula I in high purity and yield, and recovering unreacted benzene substrate for re-use.

iv. separation of the alkylsulfonic acid from the carboxylic acid and water by conventional techniques such as distillation, and recovery and re-use of the alkylsulfonic acid and carboxylic acid.

In various embodiments, the alkyl sulfonic acid is selected from the group consisting of methane sulfonic acid, ethane sulfonic acid, propane sulfonic acid and the like, and is preferably methane sulfonic acid.

In one particular embodiment of the present disclosure, the substituted benzene of Formula II is contacted with a carboxylic acid of Formula IIIa in presence of alkyl sulfonic acid of Formula IV which acts as a catalyst cum solvent/contacting medium;

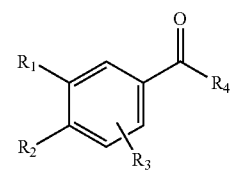

I

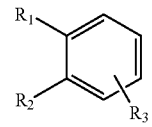

II wherein $R_1$, $R_2$ and $R_3$ are independent of each other, $R_1$ represents H, R or —OR, wherein R is a substituted or unsubstituted $C_1$-$C_4$ alkyl group, substituted or unsubstituted $C_3$-$C_6$ cycloalkyl group, $R_2$ represents hydroxy group —OH, or alkoxy group —OR, wherein R is a substituted or unsubstituted $C_1$-$C_4$ alkyl group, substituted or unsubstituted $C_3$-$C_6$ cycloalkyl group, or where $R_1$ and $R_2$ together jointly forms an alkylenedioxy group represented by —O—$(CH_2)_n$—O— wherein n is 1, 2 or 3, and $R_3$ is a substituent at any position of aromatic ring other than position 1, 3 and 4 and represents H, R, —OR, wherein R is a substituted or unsubstituted $C_1$-$C_4$ alkyl group or substituted or unsubstituted $C_3$-$C_6$ cycloalkyl group, $NH_2$ or SH, IIIa

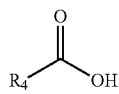

wherein $R_4$ represents, $R_6$, $XR_6$, (wherein $R_6$ is a substituted or unsubstituted $C_1$-$C_5$ alkyl group and X represents Cl, Br or Iodine substituted on $C_1$-$C_8$ carbon) or Ar—($R_6$, $OR_6$, OH or X substituted phenyl & naphthyl rings).

IV

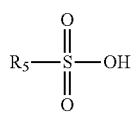

wherein $R_5$ represents an alkyl group such as methyl, ethyl or propyl,
wherein water molecules generated as a by-product is absorbed by the alkylsulfonic acid thereby enabling higher conversion of the substituted benzene of Formula II, and in high yield and giving the said product of Formula I having high purity.

High purity herein refers to over 90% based on Gas Chromatography (GC) analysis.

High yield herein refers to over 90% w/w of the substituted benzene of Formula II consumed in the reaction.

In one exemplary embodiment, anisole is reacted with propionic acid using methyl sulfonic acid hereinafter also referred as MSA as a catalyst cum solvent/contacting medium to give 4-methoxy propiophenone. The schematic representation is illustrated herein below:

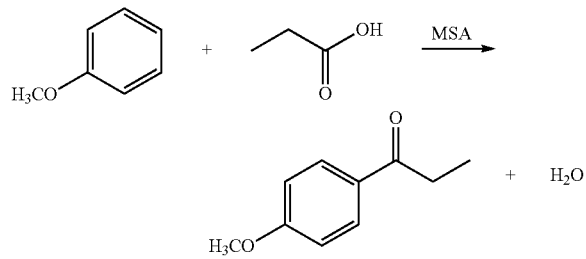

In another particular embodiment of the present disclosure, the substituted benzene substrate of Formula II is contacted with a carboxylic acid anhydride of Formula IIIb using alkyl sulfonic acid as catalyst cum solvent/contacting medium, wherein the carboxylic anhydride is consumed during acylation of the organic benzene substrate generating the corresponding carboxylic acid molecule that can further react with another substrate molecule.

In one exemplary embodiment, anisole is reacted with propionic anhydride using MSA as catalyst cum solvent/contacting medium to give 4-methoxy propionone, and the propionic acid liberated in the reaction can further react with another molecule of anisole to give 4-methoxy propionone. The schematic representation is illustrated herein below:

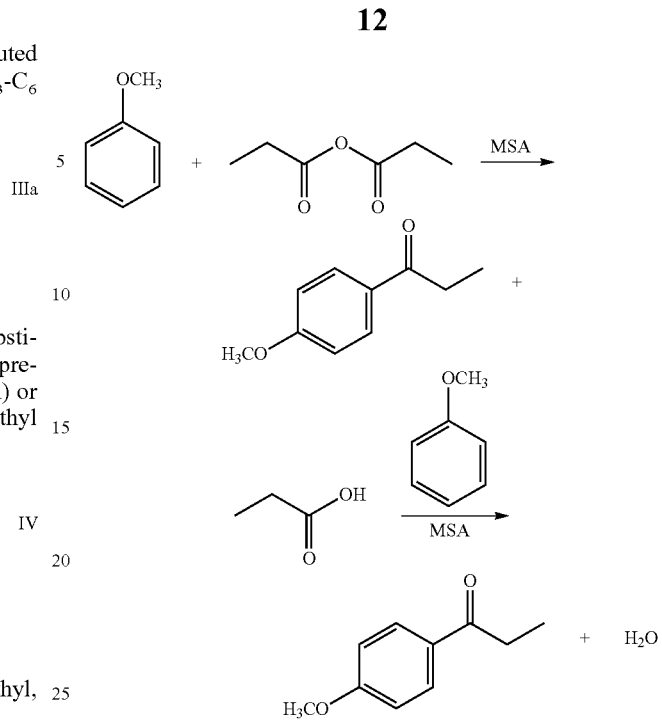

In another particular embodiment of the present disclosure, the substituted benzene substrate of Formula II is contacted with a mixture of carboxylic acid of formula IIIa and carboxylic acid anhydride of formula IIIb, using alkyl sulfonic acid as catalyst cum solvent/contacting medium.

It may be noted that either reactant, the substituted benzenes of Formula II or the carboxylic acid and/or carboxylic acid anhydride of Formula IIIa and IIIb, may be used as the limiting reactant and this choice can respond to other considerations, such as which is the more costly reactant to provide and which is more readily separated or removed to an acceptable level from the product. Generally, the mole ratio of the carboxylic acid to the substituted benzenes of Formula II is in the range of about 0.2 to about 1.2, and more typically, the carboxylic acid and substituted benzenes of Formula II are initially present in the range of about 0.3 to about 1.0 mole ratio. In a preferred embodiment, the carboxylic acid is present in the range of about 0.4 to about 0.6 moles per mole of substituted benzenes of Formula II on a molar basis. The mole ratio of the carboxylic acid anhydride to the substituted benzenes of Formula II is in the range of about 0.2 to about 1.2, and more typically, the carboxylic acid anhydride and substituted benzenes of Formula II are initially present in the range of about 0.4 to about 1.1 mole ratio. In a preferred embodiment, the carboxylic acid anhydride is present in the range of about 0.6 to about 1.0 moles per mole of substituted benzenes of Formula II on a molar basis.

The reaction temperature should be sufficient for the reaction to proceed at a practical rate. Suitable and optimal reaction temperatures depend on a number of other parameters, including the concentrations and reactivities of the specific reactants, nature of solvent/contacting medium, nature and strength of the strong protic acid and can be readily determined by routine experimentation. In typical embodiments, the reaction is conducted at a temperature in the range from about −20° C. to 120° C., preferably from about 0° C. to 70° C.

The order of addition of the reaction components is not critical. All the reaction components can be added prior to any heating to the reaction temperature or one or more components may be added when the other components have been brought to the desired reaction temperature. The preferred order of addition for any specific embodiment can be determined by routine experimentation with a view towards both reaction performance and chemical engineering considerations.

A specific embodiment of the present invention disclosed herein is the use of methane sulfonic acid as catalyst cum solvent/contacting medium, and the recovery of methane sulfonic acid from the aqueous solution obtained during the workup by distillation, whereby the water and/or carboxylic acid are separated to recover the methane sulfonic acid in substantial quantity (greater than 90%) and purity (greater than 98%). The said recovered methane sulfonic acid can be reused for the acylation purpose in future batches.

In another specific embodiment of the present invention, the compound of Formula IIa, for example methylenedioxybenzene, is reacted with propionic anhydride of Formula IIIc using MSA as a solvent/contacting medium to give a compound of Formula Ia, also known as 3,4-methylenedioxypropiophenone, which is used as intermediate to manufacture isosafrole and/or dihydrosafrole. The MSA and the propionic acid generated as by-product is substantially recovered by the process disclosed herein before, and the MSA is reused in subsequent batches. The schematic representation is illustrated herein below:

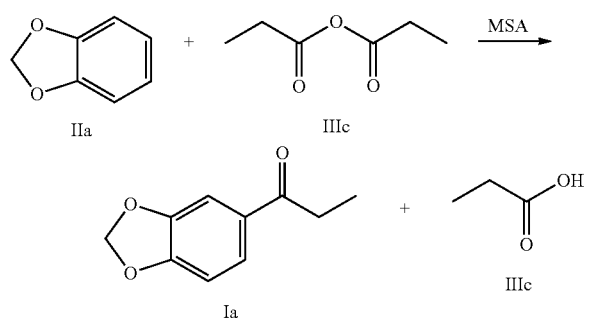

In yet another specific embodiment of the present invention, the aromatic compound of Formula IIb is contacted by carboxylic acid of Formula IIId using MSA as catalyst cum solvent to give the corresponding compound of Formula Ib. The schematic representation is illustrated herein below:

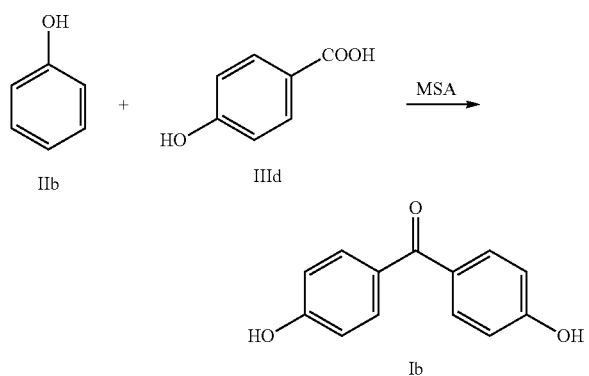

EXAMPLES

The present disclosure is further explained in the form of following examples. However, it is to be understood that the foregoing examples are merely illustrative and are not to be taken as limitations upon the scope of the invention. Various changes and modifications to the disclosed embodiments will be apparent to those skilled in the art. Such changes and modifications may be made without departing from the scope of the invention.

Example-1: Preparation of 4-Methoxy Acetophenone

Methanesulfonic acid (MSA, 768 g), Acetic acid (30 g) and Anisole (108 g) were charged into a 1 liter reaction flask. The mixture was stirred for 8 hrs at 45° C. After completion of the reaction, the reaction mass was diluted with water and product and unreacted Anisole was extracted using Toluene. The Toluene layer was distilled to recover 60 g unreacted Anisole and obtain 48 g 4-Methoxy acetophenone (GC purity>98%, yield 100% w/w on Anisole consumed). The aqueous layer was distilled to recover 729 g of MSA (purity>98%) which was reused in subsequent batches.

Example-2: Preparation of 4-Methoxy Propiophenone

Methanesulfonic acid (MSA, 768 g), Propionic acid (37 g) and Anisole (108 g) were charged into a 1 liter reaction flask. The mixture was stirred for 8 hrs at 45° C. After completion of the reaction, the reaction mass was diluted with water and product and unreacted Anisole was extracted using Toluene. The Toluene layer was distilled to recover 56 g of unreacted Anisole and obtain 58 g of 4-Methoxy propiophenone (GC purity>98%, yield 112% w/w on Anisole consumed). The aqueous layer was distilled to recover 730 g of MSA (purity>98%) which was reused in subsequent batches.

Example-3: Preparation of 4-Methoxy Propiophenone

Methane sulfonic acid (MSA, 768 g), Propionic acid (74 g) and Anisole (108 g) were charged into a 1 liter reaction flask. The mixture was stirred for 8 hrs at 45° C. After completion of the reaction, the reaction mass was diluted with water and product and unreacted Anisole was extracted using Toluene. The Toluene layer was distilled to recover 51 g of unreacted Anisole and obtain 64 g of 4-Methoxy propiophenone (GC purity>98%, yield 115% w/w on Anisole consumed). The aqueous layer was distilled to recover 32 g of Propionic acid (purity>98%) and 730 g of MSA (purity>98%) which was reused in subsequent batches.

Example-4: Preparation of 4-Methoxy Propiophenone

Methane sulfonic acid (MSA, 1152 g), Propionic acid (89 g) and Anisole (108 g) were charged into a 1 liter reaction flask. The mixture was stirred for 8 hrs at 45° C. After completion of the reaction, the reaction mass was diluted with water and product and unreacted Anisole was extracted using Toluene. The Toluene layer was distilled to recover 46 g of unreacted Anisole and obtain 71 g of 4-Methoxy propiophenone (GC purity>98%, yield 115% w/w on Anisole consumed). The aqueous layer was distilled to recover 40 g of Propionic acid (GC purity>99%) and 1095 g of MSA (purity>98%) which was reused in subsequent batches.

Example-5: Preparation of 4-Methoxy Propiophenone

Methane sulfonic acid (MSA, 1536 g), Propionic acid (89 g) and Anisole (108 g) were charged into a 1 liter reaction flask. The mixture was stirred for 8 hrs at 45° C. After completion of the reaction, the reaction mass was diluted with water and product and unreacted Anisole was extracted using Toluene. The Toluene layer was distilled to recover 36 g of unreacted Anisole and obtain 84 g of 4-Methoxy propiophenone (GC purity>98%, yield 117% w/w on Anisole consumed). The aqueous layer was distilled to recover 34 g of Propionic acid (GC purity>99%) and 1462 g of MSA (purity>98%) which was reused in subsequent batches.

Example-6: Preparation of 4-Methoxy Propiophenone

Methane sulfonic acid (MSA, 1920 g), Propionic acid (82 g) and Anisole (108 g) were charged into a 1 liter reaction flask. The mixture was stirred for 8 hrs at 45° C. After completion of the reaction, the reaction mass was diluted with water and product and unreacted Anisole was extracted using Toluene. The Toluene layer was distilled to recover 24 g of unreacted Anisole and obtain 100 g of 4-Methoxy propiophenone (GC purity>98%, yield 119% w/w on Anisole consumed). The aqueous layer was distilled to recover 19 g of Propionic acid (GC purity>99%) and 1825 g of MSA (purity>98%) which was reused in subsequent batches.

Example-7: Preparation of 4-Methoxy Phenyl Butanone

Methanesulfonic acid (MSA, 768 g), Butanoic acid (44 g) and Anisole (108 g) were charged into a 1 liter reaction flask. The mixture was stirred for 8 hrs at 45° C. After completion of the reaction, the reaction mass was diluted with water and product and unreacted Anisole was extracted using Toluene. The Toluene layer was distilled to recover 55 g of unreacted Anisole and obtain 68 g of 4-Methoxy phenyl butanone (GC purity>98%, yield 129 w/w % on Anisole consumed). The aqueous layer was distilled to recover 728 g of MSA (purity>98%) which was reused in subsequent batches.

Example-8: Preparation of 4-Methoxy Phenyl Hexanone

Methanesulfonic acid (MSA, 768 g), Hexanoic acid (58 g) and Anisole (108 g) were charged into a 1 liter reaction flask. The mixture was stirred for 8 hrs at 45° C. After completion of the reaction, the reaction mass was diluted with water and product and unreacted Anisole was extracted using Toluene. The Toluene layer was distilled to recover 56 g unreacted Anisole and obtain 73 g 4-Methoxy phenyl hexanone (GC purity>98%, yield 129 w/w % on Anisole consumed). The aqueous layer was distilled to recover 729 g of MSA (purity>99%) which was reused in subsequent batches.

Example-9: Preparation of 4-Methoxy Propiophenone

Methanesulfonic acid (MSA, 768 g), propionic anhydride (39 g), propionic acid (30 g) and Anisole (108 g) were charged into a 1 liter reaction flask. The mixture was stirred for 8 hrs at 45° C. After completion of the reaction, the reaction mass was diluted with water and product and unreacted Anisole was extracted using Toluene. The Toluene layer was distilled to recover 45 g of unreacted Anisole and obtain 71 g 4-Methoxy propiophenone (GC purity>98%, yield 113% w/w on Anisole consumed). The aqueous layer was distilled to recover 730 g of MSA (purity>98%) which was reused in subsequent batches.

Example-10: Preparation of 4-Methoxy Propiophenone

Methanesulfonic acid (MSA, 768 g), Propionic anhydride (65 g) and Anisole (108 g) were charged into a 1 liter reaction flask. The mixture was stirred for 8 hrs at 45° C. After completion of the reaction, the reaction mass was diluted with water and product and unreacted Anisole was extracted using Toluene. The Toluene layer was distilled to recover 33 g of unreacted Anisole and obtain 85 g of 4-Methoxy propiophenone (GC purity>98%, yield 114% w/w on Anisole consumed). The aqueous layer was distilled to recover 730 g of MSA (purity>98%) which was reused in subsequent batches and 25 g of Propionic acid (GC purity>99%).

Example-11: Preparation of 4-Methoxy Propiophenone

Methanesulfonic acid (MSA, 768 g), Propionic anhydride (91 g) and Anisole (108 g) were charged into a 1 liter reaction flask. The mixture was stirred for 4 hrs at 45° C. After completion of the reaction, the reaction mass was diluted with water and product and unreacted Anisole was extracted using Toluene. The Toluene layer was distilled to recover 29 g of unreacted Anisole and obtain 90 g of 4-Methoxy propiophenone (GC purity>98%, yield 114% w/w on Anisole consumed). The aqueous layer was distilled to recover 730 g of MSA (purity>98%) which was reused in subsequent batches and 38 g of Propionic acid (GC purity>99%).

Example-12: Preparation of 4-Methoxy Propiophenone

Methanesulfonic acid (MSA, 768 g), Propionic anhydride (130 g) and Anisole (108 g) were charged into a 1 liter reaction flask. The mixture was stirred for 3 hrs at 45° C. After completion of the reaction, the reaction mass was diluted with water and product and unreacted Anisole was extracted using Toluene. The Toluene layer was distilled to recover 12 g of unreacted Anisole and obtain 110 g of 4-Methoxy propiophenone (GC purity>98%, yield 115% w/w on Anisole consumed). The aqueous layer was distilled to recover 730 g of MSA (purity>98%) which was reused in subsequent batches and 70 g of Propionic acid (GC purity>99%).

Example-13: Preparation of 4-Methoxy Propiophenone

Methane sulfonic acid (MSA, 768 g) and Propionic anhydride (156 g) were charged into a 1 liter reaction flask. The mixture was cooled to 0° C. and 122 g of Anisole was added under stirring. The reaction mass was maintained at 0° C. to 5° C. for 4 hrs under stirring. After completion of the reaction, the reaction mass was diluted with water and product and unreacted Anisole was extracted using Toluene.

The Toluene layer was distilled to obtain 147 g of 4-Methoxy propiophenone (GC purity>98%, yield 136% w/w on Anisole consumed). The aqueous layer was distilled to recover 732 g of MSA (purity>98%) which was reused in subsequent batches and 86 g of Propionic acid (GC purity>99%).

Example-14: Preparation of
3,4-Methylenedioxypropiophenone

Methane sulfonic acid (MSA, 288 g) and Propionic anhydride (130 g) were charged into a 1 liter reaction flask. The mixture was cooled to 0° C. and 122 g of 3,4-Methylenedioxybenzene (MDB) was added under stirring. The reaction mass was maintained at 0° C. to 5° C. for 4 hrs under stirring. After completion of the reaction, the reaction mass was diluted with water, and the 3,4-Methylenedioxypropiophenone product and unreacted MDB was extracted using Toluene. The Toluene layer was distilled to recover 17 g of unreacted MDB and obtain 137 g of 3',4'-Methylenedioxypropiophenone (GC purity>98%, yield of 131% w/w on MDB consumed). The aqueous layer was distilled to recover 273 g of MSA (purity>98%) which was reused in subsequent batches and 63 g of Propionic acid (GC purity>99%).

Example-15: Preparation of
3,4-Methylenedioxypropiophenone

Methane sulfonic acid (MSA, 288 g) and Propionic anhydride (156 g) were charged into a 1 liter reaction flask. The mixture was cooled to 0° C. and 122 g of 3,4-Methylenedioxybenzene (MDB) was added under stirring. The reaction mass was maintained at 0° C. to 5 for 4 hrs under stirring. After completion of the reaction, the reaction mass was diluted with water, and the 3,4-Methylenedioxypropiophenone product and unreacted MDB was extracted using Toluene. The Toluene layer was distilled to recover 13 g of unreacted MDB and obtain 142 g of 3',4'-Methylenedioxypropiophenone (GC purity>98%, yield of 131% w/w on MDB consumed). The aqueous layer was distilled to recover 273 g of MSA (purity>98%) which was reused in subsequent batches and 85 g of Propionic acid (GC purity>99%).

Example-16: Preparation of
1-(4-Hydroxy-3-Methoxyphenyl) Propanone

Methane sulfonic acid (MSA, 768 g), propionic acid (37 g) and Guaiacol (124 g) were charged into a 1 liter reaction flask. The mixture was stirred for 8 hrs at 50° C. After completion of the reaction, the reaction mass was diluted with water and product and unreacted Guaicol was extracted using Toluene. The Toluene layer was distilled to recover unreacted Guaiacol and obtain 1-(4-Hydroxy-3-methoxyphenyl) propanone (GC purity>90%, yield of 120% w/w on Guaiacol consumed). The aqueous layer was distilled to recover 740 g of MSA (purity>98%) which was reused in subsequent batches and 88 g of Propionic acid (GC purity>99%).

Example-17: Preparation of
4,4-Dihydroxybenzophenone

Methane sulfonic acid (MSA, 3.8 kg), 4-hydroxybenzoic acid (0.69 kg), Phenol (0.5 kg) and Toluene (1.0 kg) were charged into a 5 liter reaction flask. The mixture was stirred for 12 hrs at 120° C. After completion of the reaction, the reaction mass was diluted with water and the product and unreacted 4-Hydroxy benzoic acid was extracted using Toluene. This was followed by crystallization of 0.52 kg of 4,4'-Dihydroxybenzophenone from the Toluene (GC purity>99%, yield of 98% w/w on Phenol). The aqueous layer was distilled to recover 3.66 kg of MSA (purity>98%) which was reused in subsequent batches.

TABLE 1

The working examples are further summarized in the table below:

| Example No. | Substrate | Qty (g) | Carboxylic Acid/Anhydride | Qty (g) | Mole per mole of substrate | ASA | Qty (g) | Mole per mole of substrate | Temp (° C.) | Rec. Substrate (g) |
|---|---|---|---|---|---|---|---|---|---|---|
| 1 | Anisole | 108 | Acetic Acid | 30 | 0.50 | MSA | 768 | 8.0 | 45 | 60 |
| 2 | Anisole | 108 | Propione Acid | 37 | 0.50 | MSA | 768 | 8.0 | 45 | 56 |
| 3 | Anisole | 108 | Propione Acid | 74 | 1.00 | MSA | 768 | 8.0 | 45 | 51 |
| 4 | Anisole | 108 | Propione Acid | 89 | 1.20 | MSA | 1152 | 12.0 | 45 | 46 |
| 5 | Anisole | 108 | Propione Acid | 89 | 1.20 | MSA | 1536 | 16.0 | 45 | 36 |
| 6 | Anisole | 108 | Propione Acid | 82 | 1.10 | MSA | 1920 | 20.0 | 45 | 24 |
| 7 | Anisole | 108 | Butanoic Acid | 44 | 0.50 | MSA | 768 | 8.0 | 45 | 55 |
| 8 | Anisole | 108 | Hexanoic acid | 58 | 0.50 | MSA | 768 | 8.0 | 45 | 56 |
| 9 | Anisole | 108 | Propionic Acid/Anhydride | 69 | 0.80 | MSA | 768 | 8.0 | 45 | 45 |
| 10 | Anisole | 108 | Propionic Anhydride | 65 | 0.50 | MSA | 768 | 8.0 | 45 | 33 |
| 11 | Anisole | 108 | Propionic Anhydride | 91 | 0.70 | MSA | 768 | 8.0 | 45 | 29 |
| 12 | Anisole | 108 | Propionic Anhydride | 130 | 1.00 | MSA | 768 | 8.0 | 45 | 12 |
| 13 | Anisole | 108 | Propionic Anhydride | 156 | 1.20 | MSA | 768 | 8.0 | 0 to 5 | 0 |
| 14 | MDB | 122 | Propionic Anhydride | 130 | 1.00 | MSA | 288 | 3.0 | 0 to 5 | 17 |
| 15 | MDB | 122 | Propionic Anhydride | 156 | 1.20 | MSA | 288 | 3.0 | 0 to 5 | 13 |
| 16 | Guaicol | 124 | Propionic Acid | 37 | 0.50 | MSA | 768 | 8.0 | 60 | 64 |
| 17 | Phenol | 500 | 4-hydroxybenzoic acid | 690 | 0.94 | MSA | 3800 | 7.4 | 120 | 158 |

| Example No. | Product | Qty (g) | Product Yield (% molar) | Product Yield (% w/w) |
|---|---|---|---|---|
| 1 | 4-Methoxy Acetoplenone | 48 | 72% | 100% |
| 2 | 4-Methoxy propiophenone | 58 | 73% | 112% |
| 3 | 4-Methoxy propiophenone | 64 | 74% | 112% |
| 4 | 4-Methoxy propiophenone | 71 | 75% | 115% |
| 5 | 4-Methoxy propiophenone | 84 | 77% | 117% |
| 6 | 4-Methoxy propiophenone | 100 | 78% | 119% |

TABLE 1-continued

The working examples are further summarized in the table below:

| | | | | |
|---|---|---|---|---|
| 7 | 4-methoxy phenyl butanone | 68 | 78% | 128% |
| 8 | 4-methoxy phenyl hexanone | 73 | 74% | 140% |
| 9 | 4-Methoxy propiophenone | 71 | 74% | 113% |
| 10 | 4-Methoxy propiophenone | 85 | 75% | 113% |
| 11 | 4-Methoxy propiophenone | 90 | 75% | 114% |
| 12 | 4-Methoxy propiophenone | 110 | 75% | 115% |
| 13 | 4-Methoxy propiophenone | 147 | 90% | 136% |
| 14 | 3,4-Methylenedioxypropiophenone | 137 | 89% | 130% |
| 15 | 3,4-Methylenedioxypropiophenone | 142 | 89% | 130% |
| 16 | 1-(4-Hydroxy-3-methoxyphenyl) propanone | 72 | 83% | 120% |
| 17 | 4,4-Dihydroxybenzophenone | 520 | 67% | 152% |

Note:
Product Yield is calculated on weight of Substrate consumed in the reaction Advantages Of The Present Invention The inventors of the present invention have developed an improved process to solve the technical problems as mentioned herein above, with the inventive feature of using an alkyl sulfonic acid as a catalyst cum solvent/contacting medium to carry out acylation of the organic substrates of Formula II using carboxylic acid and/or the corresponding carboxylic anhydrides of Formula IIIa and IIIb, having the following advantages:

1. The method disclosed herein can be used for the preparation of substituted aryl ketones of Formula I in substantially pure form in high yield, from the corresponding substituted benzenes of Formula II.
2. The method disclosed herein has the advantage of eliminating the use of conventional Lewis acid catalysts and the generation of toxic by-products formed when using conventional acylation techniques, since the alkyl sulfonic acid used as the solvent/contacting medium also acts as catalyst for said reaction.
3. The alkyl sulfonic acid used as solvent/contacting medium also acts as an effective absorbing medium for water molecules liberated during the acylation thereby taking the reaction forward without any extra unit operation for the simultaneous removal of water to take the reaction forward.
4. The alkyl sulfonic acid together with the unreacted carboxylic acid are easily separated from the substituted aryl ketones of Formula I and the unreacted substituted benzenes of Formula II by dilution with water, whereby the substituted aryl ketones of Formula I and the unreacted substituted benzenes of Formula II remain in the organic phase, and the alkyl sulfonic acid together with unreacted carboxylic acid are separated in the aqueous phase.
5. The alkyl sulfonic acid and unreacted carboxylic acid are substantially recovered using conventional techniques such as distillation, and the alkyl sulfonic acid can be reused for the same purpose multiple times, without significant loss of activity, thereby making process economically viable.

We claim:
1. A process for preparation of an aryl ketone of Formula I comprising:
   i. contacting substituted benzene of Formula II with a carboxylic acid of Formula Ma and/or a carboxylic acid anhydride of Formula IIIb in presence of an alkyl sulfonic acid used in an amount ranging from 3.0 to 16.0 moles per mole of the substituted benzene of formula II acting as catalyst cum solvent/contacting medium, to form in a reaction mass an aryl ketone of Formula I,

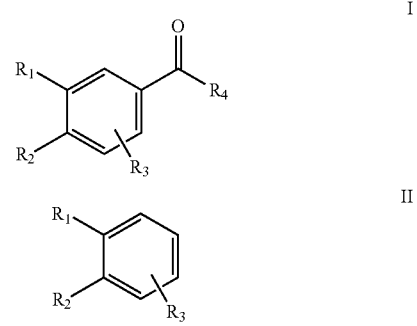

wherein Ri R2 and R3 are independent of each other,
Ri represents H, R or —OR, wherein R is a substituted or unsubstituted C1-C4 alkyl group, substituted or unsubstituted C3-C6 cycloalkyl group,
R2 represents hydroxy group —OH, or alkoxy group —OR, wherein R is a substituted or unsubstituted C1-C4 alkyl group, substituted or unsubstituted C3-C6 cycloalkyl group,
or where Ri and R2 together jointly form an alkylenedioxy group represented by—0-(CH2)n-0-wherein n is 1, 2 or 3,
and R3 is a substituent at any position of aromatic ring other than position 1, 3 and 4 and represents H, R, —OR, wherein R is a substituted or unsubstituted C1-C4 alkyl group or substituted or unsubstituted C3-C6 cycloalkyl group, NH2 or SH,

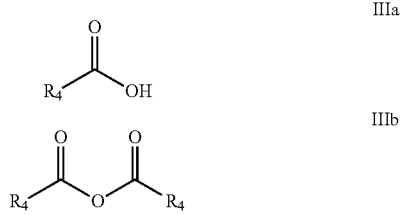

wherein R4 represents, 5, XRS, (wherein 5 is a substituted or unsubstituted Ci-C8 alkyl group and X represents Cl, Br or Iodine substituted on Ci-C8 carbon) or Ar-(R6, OR5, OH or X substituted phenyl & naphthyl rings);

ii. adding water to the reaction mass to form an aqueous phase and an organic phase, wherein the organic phase comprises unreacted substituted benzene of formula II and the thus formed aryl ketone of formula I, and the aqueous phase comprises the alkyl sulfonic acid and unreacted carboxylic acid;

iii. recovering unreacted substituted benzene of formula II and obtaining the thus formed aryl ketone of formula I from the organic phase; and iv. recovering the alkyl sulfonic acid from the aqueous phase.

2. The process as claimed in claim 1, wherein the alkyl sulfonic acid is selected from the group consisting of methane sulfonic acid, ethane sulfonic acid, propane sulfonic acid, or a mixture thereof.

3. The process as claimed in claim 2, wherein the alkyl sulfonic acid is methane sulfonic acid.

4. The process as claimed in claim 1, wherein the carboxylic acid of Formula Ma is used in an amount ranging from 0.2 to 1.2 moles per mole of the substituted benzene of Formula II.

5. The process as claimed in claim 1, wherein the carboxylic acid anhydride of Formula IIIb is used in an amount ranging from 0.2 to 1.2 moles per mole of the substituted benzene of Formula II.

6. The process as claimed in claim 1, wherein the substituted benzene of Formula II is 3, 4-methylenedioxybenzene and the corresponding aryl ketone of Formula I is 3,4-methylenedioxypropiophenone.

7. The process as claimed in claim 1, wherein the substituted benzene of Formula II is guaiacol and the corresponding aryl ketone of Formula I is 1-(4-hydroxy-3-methoxyphenyl) propanone.

8. The process as claimed in claim 1, wherein the substituted benzene of Formula II is anisole and the corresponding aryl ketone of Formula I is 4-methoxy propiophenone.

9. The process as claimed in claim 1, wherein the recovered unreacted substituted benzene of formula II and the recovered alkyl sulfonic acid are re-used in a subsequent process for preparation of the aryl ketone of Formula T.

\* \* \* \* \*